US012616371B2

(12) United States Patent
Redford

(10) Patent No.:  US 12,616,371 B2
(45) Date of Patent:  May 5, 2026

(54) REAL-TIME TRACHEAL MAPPING USING OPTICAL COHERENCE TOMOGRAPHY AND ARTIFICIAL INTELLIGENCE

(71) Applicant: Lazzaro Medical, Inc., Boulder, CO (US)

(72) Inventor: Ryan Redford, Irvine, CA (US)

(73) Assignee: BLACK FUR BIOMEDICAL LLC, Irvine, CA (US)

( * ) Notice: Subject to any disclaimer, the term of this patent is extended or adjusted under 35 U.S.C. 154(b) by 114 days.

(21) Appl. No.: 18/601,459

(22) Filed: Mar. 11, 2024

(65) Prior Publication Data

US 2024/0298898 A1    Sep. 12, 2024

Related U.S. Application Data

(60) Provisional application No. 63/451,467, filed on Mar. 10, 2023.

(51) Int. Cl.
A61B 5/00        (2006.01)
G06T 5/60        (2024.01)
(Continued)

(52) U.S. Cl.
CPC ............. A61B 5/0066 (2013.01); G06T 5/60 (2024.01); G06T 5/70 (2024.01); G06T 5/80 (2024.01);
(Continued)

(58) Field of Classification Search
CPC ... A61B 5/0066; A61B 5/6852; A61B 5/7267; G06T 5/60; G06T 5/70; G06T 5/80;
G06T 7/0012; G06T 7/70; G06T 2200/04;
G06T 2207/10101; G06T 2207/20076;
G06T 2207/20081; G06T 2207/20084;
G06T 2207/30028; G06T 2207/30061;
G06T 2207/30101; G06T 2207/30004
See application file for complete search history.

(56) References Cited

U.S. PATENT DOCUMENTS

| | | | | |
|---|---|---|---|---|
| 9,286,673 B2 * | 3/2016 | Begin | ......................... | G06T 5/80 |
| 10,058,284 B2 * | 8/2018 | Hoseit | ...................... | A61B 8/12 |

(Continued)

OTHER PUBLICATIONS

International Search Report and Written Opinion issued in PCT/US2024/019396, dated Jul. 9, 2024, 8 pgs.

(Continued)

*Primary Examiner* — Joel Lamprecht
(74) *Attorney, Agent, or Firm* — HAYES SOLOWAY P. C.

(57) ABSTRACT

A system and method are disclosed for real-time mapping of a target hollow internal body structure each as the trachea using ultrafast swept-source optical coherence tomography (SS-OCT) and artificial intelligence (AI). The system includes an SS-OCT imaging device that captures high-resolution 3D images of the trachea at very high frame rates, and an AI module that analyzes and interprets the images in real time. The AI module can recognize patterns and features in the images and make predictions about the tracheal anatomy or disease status. The system can provide a detailed, up-to-date model of the trachea in real time, and can be used for a variety of applications including diagnosis, surgery, and monitoring.

13 Claims, 1 Drawing Sheet

(51) Int. Cl.

| | | |
|---|---|---|
| *G06T 5/70* | (2024.01) | |
| *G06T 5/80* | (2024.01) | |
| *G06T 7/00* | (2017.01) | |
| *G06T 7/70* | (2017.01) | |

(52) U.S. Cl.

CPC .............. *G06T 7/0012* (2013.01); *G06T 7/70* (2017.01); *G06T 2200/04* (2013.01); *G06T 2207/10101* (2013.01); *G06T 2207/20076* (2013.01); *G06T 2207/20081* (2013.01); *G06T 2207/20084* (2013.01); *G06T 2207/30028* (2013.01); *G06T 2207/30061* (2013.01); *G06T 2207/30101* (2013.01)

(56) References Cited

U.S. PATENT DOCUMENTS

| | | |
|---|---|---|
| 10,980,955 B2 | 4/2021 | Nawn et al. |
| 2013/0182260 A1 | 7/2013 | Bonnema et al. |
| 2021/0177282 A1 | 6/2021 | Ahmed et al. |
| 2022/0284606 A1 | 9/2022 | Li et al. |

OTHER PUBLICATIONS

Chen et al., "Deep Learning Artificial Intelligence to Predict the Need for Tracheostomy in Patients of Deep Neck Infection Based on Clinical and Computed Tomography Findings—Preliminary Data and a Pilot Study", Diagnostics 2022, 12(8), 1943, Aug. 12, 2022, https://doi.org/10.3390/diagnostics12081943, 9 pgs.
Su et al., "Real-time swept source optical coherence tomography imaging of the human airway using a microelectromechanical system endoscope and digital signal processor", J Biomed Opt. 2008, 13(3), 030506, Nov. 16, 2009, doi: 10.1117/1.2938700, 8 pgs.
Mikami et al., "Ultrafast optical imaging technology: principles and applications of emerging methods", Nanophotonics, vol. 5, Issue 4, Oct. 20, 2016, https://doi.org/10.1515/nanoph-2016-0026, 26 pgs.
"Optical coherence tomography", Wikipedia, version from Dec. 30, 2022, https://en.wikipedia.org/w/index.php?title=Optical_coherence_tomography&oldid=1130501530, 18 pgs.

* cited by examiner

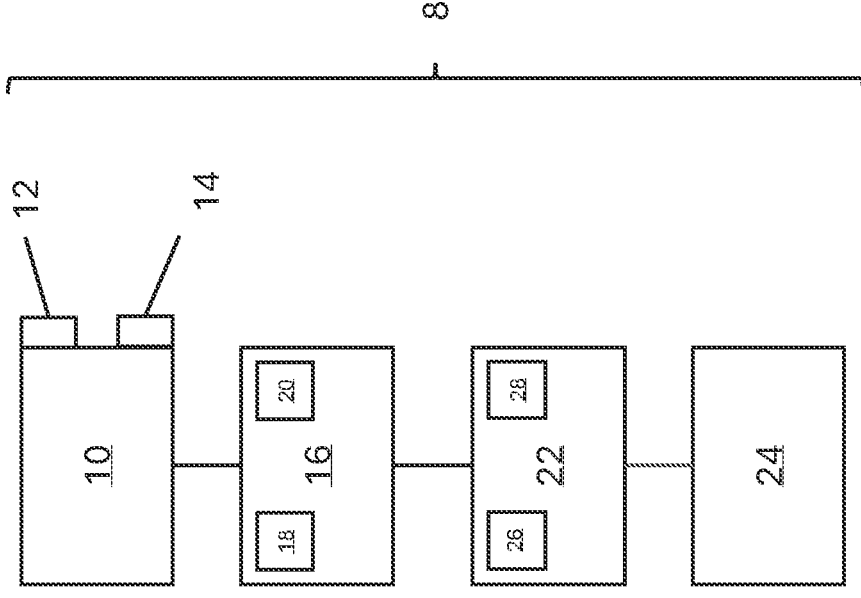

REAL-TIME TRACHEAL MAPPING USING OPTICAL COHERENCE TOMOGRAPHY AND ARTIFICIAL INTELLIGENCE

CROSS REFERENCE TO RELATED APPLICATION

This application claims priority from U.S. Provisional Application Ser. No. 63/451,467, filed Mar. 10, 2023, the contents of which are incorporated herein in their entirety.

TECHNICAL FIELD

The present disclosure relates to medical imaging and systems and methods for medical imaging. The disclosure has particular applicability in the field of medical imaging of target hollow internal body structures of humans and animals such as the trachea and will be described in connection with such utility, although other utilities are contemplated.

BACKGROUND AND SUMMARY

The trachea is a vital organ that carries air to and from the lungs. It is susceptible to a variety of diseases and disorders, and accurate, real-time mapping of the trachea can be helpful for diagnosis, treatment, and monitoring of disease advancement and effect of treatment. Computed tomography currently is the modality of choice for imaging the trachea and bronchi. Computed tomography provides clear anatomical details on cross-sectional imaging and provides a direct display of tracheal bronchial anatomy. Magnetic resonance imaging (MRI) also has been used for imaging the trachea and bronchi. However, current imaging techniques of computed tomography (CT) and magnetic resonance imaging (MRI) are not well suited for real-time imaging of the trachea due to their low temporal resolution.

Optical coherence tomography (OCT) is an image technique that uses low-coherence light, typically near-infrared light, to capture micrometer-resolution, two and three-dimension images from within optical scattering media such as biological tissue. OCT traditionally has been employed in non-invasive imaging techniques based on optical coherence that has been developed to visualize vascular networks in the human retina, choroid, skin, etc. OCT employs low-coherence interferometry to measure changes in back scattered light to differentiate areas of blood flow from the areas of static flow.

Swept-source ultra-fast optical coherence tomography (UF-OCT) can provide high-resolution 3D images a hollow target internal body structures such as the trachea at very high frame rates. However, manual interpretation of UF-OCT images can be time-consuming and subjective, and there is a need for a more efficient and accurate method for analyzing and interpreting the images in real time.

The present disclosure addresses these and other needs by providing a system and method for real-time mapping of a human or animal hollow target internal body structure such as the trachea using OCT/UF-OCT and artificial intelligence (AI). The system includes an UF-OCT imaging device that captures high-resolution 3D images of a hollow target internal body structure, e.g., the trachea, at very high frame rates, typically 1 MHz to 1000 GHz, and an AI module that analyzes and interprets the images in real time. The AI module can recognize patterns and features in the images and make predictions about the hollow internal body structure anatomy or disease status. The system can provide a detailed, up-to-date 3D images of the hollow internal body structure in real time and can be used for a variety of applications including diagnosis, surgery, and monitoring.

The present disclosure in one aspect provides a system for real-time mapping of a hollow target body structure, comprising: an ultrafast imaging device configured to capture 3D images of the hollow target internal body structure at very high frame rates; an artificial intelligence (AI) module configured to analyze and interpret the 3D images in real time; and configured to display the 3D images and the AI predictions in real time.

In one aspect the target body structure is a hollow organ such as the trachea.

In another aspect the ultrafast imaging device is an ultra-fast (UF) swept-source optical coherence tomography (SS-OCT) device.

In a further aspect the AI module is a machine learning model trained on a dataset of SS-OCT images and corresponding hollow target body structure anatomy or disease labels.

In yet another aspect the display is configured to display the 3D images of the hollow target body structure and the AI predictions on the same device as the ultrafast imaging device.

The system also may comprise a database configured to store the 3D images of the hollow target body structure and the AI predictions.

In a further aspect of the disclosure the hollow target internal body structure is selected from the group consisting of internal body structures of the mouth and throat such as the trachea, lungs, large and small intestines, bladder, nasal and ear canals, blood vessels and arteries.

The present disclosure also provides a method for real-time mapping of a hollow target body structure such as the trachea, comprising: capturing 3D images of the hollow target body structure at very high frame rates using an ultrafast optical coherence tomography (UF-OCT) imaging device; analyzing and interpreting the 3D images of the target body structure in real time using an artificial intelligence (AI) module; and displaying the 3D images of the target body structure and the AI predictions in real time.

In a further aspect of the disclosure the AI module is a machine learning model trained on a dataset of a swept-source optical coherence tomography (SS-OCT) images and corresponding hollow target body structure anatomy or disease labels.

In yet another aspect of the disclosure the AI module is a machine learning model trained on a dataset of OCT images and corresponding hollow target internal body structure anatomy or disease labels.

Yet another aspect of the disclosure comprises real-time mapping of the hollow target body structure using UF-OCT of a hollow internal body structure, with AI for one or more of: diagnosis, surgery, and monitoring.

The present disclosure also provides an article of manufacturing comprising a computer-readable medium having computer readable program code disposed therein, which when executed by a processor, cause the processor to perform the method for real-time mapping of a hollow target body structure such as the trachea, comprising: capturing 3D images of the hollow target body structure at very high frame rates using an ultrafast optical coherence tomography imaging device (UF-OCT); analyzing and interpreting the 3D images of the hollow target body structure in real time using an artificial intelligence (AI) module; and displaying the 3D images of the hollow target body structure and the AI predictions in real time.

In a further aspect of the disclosure the hollow target internal body structure is selected from the group consisting of internal body structures of the mouth and throat such as the trachea, lungs, large and small intestines, bladder, nasal and ear canals, blood vessels and arteries.

In yet a further aspect of the disclosure the computer-readable medium is utilized for storing instructions that, when executed by a processor, cause the process to perform the method described herein.

The present disclosure also provides an article of manufacturing comprising a computer-readable medium having computer readable program code disposed therein, which when executed by a processor, cause the processor to perform the method further comprises capturing the 3D images of a hollow target body structure such as the trachea and the AI predictions in a database according to the equation: $D[I(x, y, z, t), p(a|I)]=(x, y, z, t, a)$ where D[ ] is a function that stores the image $I(x, y, z, t)$ and the AI prediction $p(a|I)$ in the database, and $(x, y, z, t, a)$ is a tuple representing the position, time, and prediction.

The present disclosure also provides a computer-readable medium storing instructions that, when executed by a processor, cause the processor to perform the method for real-time mapping of a hollow target body structure such as the tracheas comprising capturing 3D images of the hollow target body structure at very high frame rates using an ultrafast imaging device; analyzing and interpreting the 3D images in real time using an artificial intelligence (AI) module; displaying the 3D images and the AI predictions in real time.

The present disclosure also provides for a method for real-time mapping of the trachea using ultrafast swept-source optical coherence tomography (SS-OCT) and artificial intelligence (AI), comprising: capturing 3D images of the trachea at very high frame rates using an ultrafast OCT device, according to the equation: $I(x, y, z, t)=f(O(x, y, z, t))$, where $I(x, y, z, t)$ is the 3D image of the trachea at position $(x, y, z)$ and time t, $O(x, y, z, t)$ is the interferometric signal from the ultrafast OCT device at position $(x, y, z)$ and time t, and f( ) is a function that maps the interferometric signal to the image; and analyzing and interpreting the 3D images in real time using an AI module, according to the equation: $p(a|I)=\text{argmax } f\_\theta(I)$, where $p(a|I)$ is the probability of the AI prediction a given the image I, $f\_\theta( )$ is a machine learning model with parameters $\theta$, and argmax denotes the argument that maximizes the model output; and displaying the 3D images and the AI predictions in real time.

The present disclosure also provides for storing the 3D images and the AI predictions in a database according to the equation: $D[I(x, y, z, t), p(a|I)]=(x, y, z, t, a)$ where D[ ] is a function that stores the image $I(x, y, z, t)$ and the AI prediction $p(a|I)$ in the database, and $(x, y, z, t, a)$ is a tuple representing the position, time, and prediction.

In yet a further aspect of the present disclosure the real-time mapping of the trachea for one or more of: diagnosis, surgery, and monitoring, according to the equation: $U(I, p(a|I))=(d, s, m)$ where U( ) is a function that maps the image I and the AI prediction $p(a|I)$ to the diagnostic, surgical, and monitoring outputs (d, s, m).

In yet another further aspect of the present invention sparse coding-based image analysis: $a=\text{argmin } \Sigma|I-D*a|^2+\lambda\Sigma|a|$ where a is the coefficient vector for the image I, D is the dictionary matrix, and $\lambda$ is a constant, and wherein coefficient vector optionally is obtained by minimizing the reconstruction error between the image I and its reconstruction D*a, using a sparsity-promoting regularization term $\lambda\Sigma|a|$.

In another aspect of the present disclosure a dictionary learning-based image analysis: $D=\text{argmin } \Sigma\Sigma|I-D*a|^2+\lambda\Sigma\Sigma|a|$ where D is the dictionary matrix, a is the coefficient vector for the image I, and $\lambda$ is a constant, and wherein the dictionary matrix D optionally is obtained by minimizing the reconstruction error between the image I and its reconstruction D*a, using a sparsity-promoting regularization term $\lambda\Sigma\Sigma|a|$.

In yet another aspect of the present disclosure deep learning-based image analysis: $f\_\theta(I)=g(h\_\theta(I))$ where $f\_\theta( )$ is a deep learning model with parameters $\theta$, I is the input image, $h\_\theta( )$ is the hidden representation of the image, and go is the output layer of the model, and wherein the model optionally is trained by minimizing a loss function $L(y, f\_\theta(I))$ that measures the difference between the true label y and the model output $f\_\theta(I)$, using stochastic gradient descent or another optimization algorithm.

In another aspect of the present disclosure geometric transformation-based image correction: $I'=T(I)$ where I is the input image, I' is the corrected image, and T( ) is a geometric transformation function that maps the image I to the corrected image I', wherein the transformation function T( ) optionally is a rotation, translation, scaling, or other type of transformation that is applied to the image I to correct for geometric distortion or other issues.

In yet a further aspect of the present disclosure an image denoising-based image correction: $I'=\text{argmin } \Sigma|I-I'|^2+\lambda\Sigma|\nabla I'|$ where I is the input image, I' is the corrected image, $\Sigma|I-I'|^2$ is the reconstruction error between the image I and its denoised version I', and $\Sigma|\nabla I'|$ is a regularization term that promotes smoothness in the image I', and wherein the corrected image I' optionally is obtained by minimizing this energy function using an optimization algorithm such as gradient descent.

In another aspect, the computer-readable medium stores instructions that, when executed by a processor, cause the processor to perform the method described herein.

DETAILED DESCRIPTION

As used herein "very high frame rates" means frame rates of 1 MHz to 1000 GHz.

The present disclosure provides is a system and method for real-time mapping of a hollow target body structure such as the trachea using ultrafast OCT and AI. The system includes an OCT imaging device configured to capture high-resolution 3D images of the hollow target body structure from inside the target body structure at very high frame rates, i.e., preferably 1 MHz to 1000 GHz, and an AI module configured to analyze and interpret the images in real time. The OCT imaging device may be a swept-source laser or other suitable ultrafast OCT imaging device and may be configured to transmit light into hollow target body structure, e.g., the trachea, and to detect the reflected or scattered light using interferometry. Using AI to predict the resulting interferometric signal is then processed to generate 3D images of the hollow target body structure with high spatial and temporal resolution.

The AI module may be a machine learning model, such as a convolutional neural network (CNN) to analyze visual imagery, or a recurrent neural network (RNN), that has been trained on a dataset of OCT images and corresponding hollow body structure anatomy or disease labels. The AI module may be configured to analyze the OCT images in real time and to make predictions about the hollow body structure anatomy or disease status. Predictions may be based on patterns and features in the images that are indicative of specific anatomic structures or pathologies.

The system may be configured to display the OCT images and the AI predictions in real time, either on a separate display device or on the same device as the OCT imaging device. The system may also be configured to store the OCT images and the AI predictions in a database for later review or analysis.

The system may be used for a variety of applications including diagnosis, surgery, and monitoring of hollow body structure such as the trachea. In the diagnostic setting, the system may be used to identify abnormalities or pathologies in the hollow body structure that may not be visible on other imaging modalities. In the surgical setting, the system may be used to guide the surgeon during procedures such as, e.g., in the case of the trachea, tracheostomy or tracheal resection. The real-time mapping capabilities of the system can help the surgeon to visualize the anatomy and to navigate within the hollow body structure more accurately. In the monitoring setting, the system may be used to track the progression of diseases or treatments over time and to detect early changes that may require intervention.

The present invention offers several advantages over prior art methods for hollow body structure imaging. By using ultrafast OCT, the system can capture high-resolution 3D images of a hollow body structure at very high frame rates, allowing it to track fast-moving or dynamic structures in real time. By using AI to analyze and interpret the images, the system can provide more accurate and objective predictions about the hollow body structure anatomy or disease status than manual interpretation. The real-time mapping capabilities of the system can also be beneficial for a variety of applications, including diagnosis, surgery, and monitoring.

BRIEF DESCRIPTION OF THE DRAWINGS

Further features and advantages of the disclosure will be seen from the following detailed description, taken in conjunction with the accompanying drawings, therein like numerals depict like parts, and wherein:

FIG. 1 is a schematic illustration of an ultra-fast optical coherence tomography (UF-OCT) imaging system employing AI in accordance with an embodiment of the present disclosure.

DETAILED DESCRIPTION OF THE DISCLOSURE

Referring to FIG. 1, the imaging system 8 in accordance with the present disclosure includes an UF-OTC probe 10 which may take the form of a catheter, endoscope or the like, configured to be inserted into a target hollow internal body structure of interest such as, for example, the trachea. A light source 12, configured to generate near-infrared light and an optical detector 14 configured to detect reflected light, a swept-source optical coherence tomography device 16 including an OTC engine 18, and an OTC controller 20. The imaging system 10 further includes a processor 22 and a display 24. The optical coherence tomography device 16 is configured to transmit light into the hollow body structure of interest, and to detect back-scattered light reflected by the target hollow internal body structure of interest.

A feature of the subject disclosure is incorporation of an artificial intelligence (AI) module 26 in the processor 22 which is configured to capture 3D images from the reflect light, analyze and interpret the 3D images in real time, and then send signals to the display 24 to display the 3D images in real time. To this end, processor 22 includes a computer-readable medium 28 storing instructions for real-time mapping hollow of the target body structure essentially in real time.

Various techniques can be used for capturing, storing and displaying the images including employing AI to analyze and interpret the 3D images in real time and send signals to the display, including but not limited to:

Capturing 3D images of the hollow target body structure at very high frame rates using an ultrafast OCT device, according to the equation:

$$I(x,y,z,t)=f(O(x,y,z,t))$$

where I(x, y, z, t) is the 3D image of the hollow target body structure at position (x, y, z) and time t, O(x, y, z, t) is the interferometric signal from the ultrafast OCT device at position (x, y, z) and time t, and f( ) is a function that maps the interferometric signal to the image;

analyzing and interpreting the 3D images of the hollow target body structure in real time using an AI module, according to the equation:

$$p(a \,|\, I) = \mathrm{argmax}\ f\_\theta(I)$$

where p(a|I) is the probability of the AI prediction a given the image I, f_θ( ) is a machine learning model with parameters θ, and argmax denotes the argument that maximizes the model output; and displaying the 3D images of the hollow target body structure and the AI predictions in real time.

Storing the 3D images of a hollow target body structure such as the trachea and the AI predictions in a database according to the equation: D[I(x, y, z, t), p(a|I)]=(x, y, z, t, a) where D[ ] is a function that stores the image I(x, y, z, t) and the AI prediction p(a|I) in the database, and (x, y, z, t, a) is a tuple representing the position, time, and prediction.

Using real-time mapping of a hollow target body structure, for one or more of: diagnosis, surgery, and monitoring, according to the equation: U(I, p(a|I))= (d, s, m) where U(is a function that maps the image I and the AI prediction p(a|I) to diagnostic, surgical, and monitoring outputs (d, s, m).

We may employ sparse coding-based image analysis of a hollow target body structure such as the trachea to represent the image I as a linear combination of a dictionary of bases and to reduce the redundancy in the representation, according to the following equation:

$$a = \mathrm{argmin} \sum |I - D*a|^2 + \lambda \sum |a|$$

where a is the coefficient vector for the image I, D is the dictionary matrix, and λ is a constant. The coefficient vectors can be obtained by minimizing the reconstruction error between the image I and its reconstruction D*a, using a sparsity-promoting regularization term $\lambda\Sigma|a|$.

We employ dictionary learning-based image analysis according to the following equation, to improve the performance of the image analysis of a hollow target body structure such as the trachea:

$$D = \text{argmin} \sum\sum |I - D^*a|^{\wedge}2 + \lambda \sum\sum |a|$$

where D is the dictionary matrix, a is the coefficient vector for the image I, and $\lambda$ is a constant. The dictionary matrix D can be obtained by minimizing the reconstruction error between the image I and its reconstruction D*a, using a sparsity-promoting regularization term $\lambda\Sigma\Sigma|a|$. This approach can be used to learn a dictionary of bases that is well-suited for the image data and to improve the performance of the image analysis.

In one embodiment we employ a method for deep learning-based image analysis of a hollow target body structure such as the trachea according to the following formula:

$$f\_\theta(I) = g(h\_\theta(I))$$

where f_θ( ) is a deep learning model with parameters θ, I is the input image, h_θ( ) is the hidden representation of the image, and g( ) is the output layer of the model. The model can be trained by minimizing a loss function L(y, f_θ(I)) that measures the difference between the true label y and the model output f_θ(I), using stochastic gradient descent or another optimization algorithm. This approach can be used to learn a hierarchical representation of the image data and to achieve state-of-the-art performance in a variety of image analysis tasks.

In another embodiment we employ a method for geometric transformation-based image correction: I'=T (I) where I is the input image, I' is the corrected image, and T( ) is a geometric transformation function that maps the image I to the corrected image I'. The transformation function T( ) may be a rotation, translation, scaling, or other type of transformation that is applied to the image I to correct for geometric distortion or other issues. This approach can be used to improve the quality and accuracy of the 3D maps of a hollow target body structure such as the trachea.

We may employ an image denoising-based image correction: I'=argmin $\Sigma|I-I'|^{\wedge}2+\lambda\Sigma|\nabla I'|$ where I is the input image, I' is the corrected image, $\Sigma|I-I'|^{\wedge}2$ is the reconstruction error between the image I and its denoised version I', and $\Sigma|\nabla I'|$ is a regularization term that promotes smoothness in the image I'. The corrected image I' can be obtained by minimizing this energy function using an optimization algorithm such as gradient descent. This approach can be used to remove noise or other artifacts from the image I and to improve the quality and accuracy of the 3D maps of a hollow target body structure such as the trachea.

While the foregoing disclosure has been made particularly in connection with the real time mapping of the trachea, the disclosure also advantageously may be used for real time of other hollow internal body structures including the mouth and throat, lungs, large and small intestines, bladder, nasal and ear canals, blood vessels, arteries, and the like.

The invention claimed is:

1. A method for real-time mapping of a human or animal hollow target internal body structure, using ultrafast swept-source optical coherence tomography (SS-OCT) and artificial intelligence (AI), comprising:

providing a system for real-time mapping of a human or animal hollow target internal body structure, said system comprising: an ultrafast imaging device configured to capture 3D images of the hollow target internal body structure at very high frame rates; an artificial intelligence (AI) module configured to analyze and interpret the 3D images in real time; a display configured to display the 3D images and the AI predictions in real time, capturing 3D images of the hollow target internal body structure at very high frame rates using an ultrafast OCT device, according to the equation:

$$I(x, y, z, t) = f(O(x, y, z, t))$$

where I(x, y, z, t) is the 3D image of the hollow target internal body structure at position (x, y, z) and time t, O(x, y, z, t) is the interferometric signal from the ultrafast OCT device at position (x, y, z) and time t, and f( ) is a function that maps the interferometric signal to the image;

analyzing and interpreting the 3D images in real time using an AI module, according to the equation:

$$p(a \,|\, I) = \text{argmax}\, f\_\theta(I)$$

where p(a|I) is the probability of the AI prediction a given the image I, f_θ( ) is a machine learning model with parameters θ, and argmax denotes the argument that maximizes the model output; and displaying the 3D images and the AI predictions in real time.

2. The method of claim 1, wherein the ultrafast imaging device is a swept-source optical coherence tomography (SS-OCT) device.

3. The method of claim 1, wherein the AI module is a machine learning model trained on a dataset of OCT images and corresponding hollow target internal body structure anatomy or disease labels.

4. The method of claim 1, further comprising storing the 3D images and the AI predictions in a database, and/or further comprising using the real-time mapping of the hollow target internal body structure for one or more of: diagnosis, surgery, and monitoring.

5. The method of claim 1, wherein the hollow target internal body structure is selected from the group consisting of internal body structures of the mouth and throat such as the trachea, lungs, large and small intestines, bladder, nasal and ear canals, blood vessels and arteries.

6. The method of claim 1, further comprising storing the 3D images and the AI predictions in a database according to the equation: D[I(x, y, z, t), p(a|I)]=(x, y, z, t, a) where D[ ] is a function that stores the image I(x, y, z, t) and the AI prediction p(a|I) in the database, and (x, y, z, t, a) is a tuple representing the position, time, and prediction.

7. The method of claim 1, further comprising using the real-time mapping of the hollow target internal body structure for one or more of: diagnosis, surgery, and monitoring, according to the equation: U(I, p(a|I))=(d, s, m) where U( ) is a function that maps the image I and the AI prediction p(a|I) to the diagnostic, surgical, and monitoring outputs (d, s, m).

8. The method of claim 1, further comprising sparse coding-based image analysis:

$$a = \operatorname{argmin} \sum |I - D^*a|^\wedge 2 + \lambda \sum |a|$$

where a is the coefficient vector for the image I, D is the dictionary matrix, and A is a constant, and wherein coefficient vector optionally is obtained by minimizing the reconstruction error between the image I and its reconstruction D*a, using a spars ity-promoting regularization term $\lambda \Sigma |a|$.

9. The method of claim 1, further comprising dictionary learning-based image analysis:

$$D = \operatorname{argmin} \sum \sum |I - D^*a|^\wedge 2 + \lambda \sum \sum |a|$$

where D is the dictionary matrix, a is the coefficient vector for the image I, and $\lambda$ is a constant, and wherein the dictionary matrix D optionally is obtained by minimizing the reconstruction error between the image I and its reconstruction D*a, using a sparsity-promoting regularization term $\lambda \Sigma \Sigma |a|$.

10. The method of claim 1, further comprising deep learning-based image analysis:

$$f\_\theta(I) = g(h\_\theta(I))$$

where f_θ( ) is a deep learning model with parameters θ, I is the input image, h_θ( ) is the hidden representation of the image, and g( ) is the output layer of the model, and wherein the model optionally is trained by minimizing a loss function L(y, f_θ(I)) that measures the difference between the true label y and the model output f_θ(I), using stochastic gradient descent or another optimization algorithm.

11. The method of claim 1, further comprising geometric transformation-based image correction: I'=T (I) where I is the input image, I' is the corrected image, and T( ) is a geometric transformation function that maps the image I to the corrected image I', wherein the transformation function T( ) optionally is a rotation, translation, scaling, or other type of transformation that is applied to the image I to correct for geometric distortion or other issues.

12. The method of claim 1, further comprising image denoising-based image correction: I'=argmin $\Sigma |I - I'|^\wedge 2 + \lambda \Sigma |\nabla I'|$ where I is the input image, I' is the corrected image, $\Sigma |I - I'|^\wedge 2$ is the reconstruction error between the image I and its denoised version I', and $\Sigma |\nabla I'|$ is a regularization term that promotes smoothness in the image I', and wherein the corrected image I' optionally is obtained by minimizing this energy function using an optimization algorithm such as gradient descent.

13. A computer-readable medium storing instructions that, when executed by a processor, cause the processor to perform the method of claim 1.

* * * * *